(12) United States Patent
Becorest et al.

(10) Patent No.: US 11,495,019 B2
(45) Date of Patent: Nov. 8, 2022

(54) SYSTEMS AND METHODS FOR OPTICAL CHARACTER RECOGNITION OF TEXT AND INFORMATION ON A CURVED SURFACE

(71) Applicant: GIVATAR, INC., San Diego, CA (US)

(72) Inventors: William E. Becorest, San Diego, CA (US); Yongkeng Xiao, San Diego, CA (US)

(73) Assignee: GIVATAR, INC., San Diego, CA (US)

( * ) Notice: Subject to any disclaimer, the term of this patent is extended or adjusted under 35 U.S.C. 154(b) by 0 days.

(21) Appl. No.: 17/216,181

(22) Filed: Mar. 29, 2021

(65) Prior Publication Data

US 2021/0303861 A1   Sep. 30, 2021

Related U.S. Application Data (60) Provisional application No. 63/001,058, filed on Mar. 27, 2020, provisional application No. 63/001,002, filed on Mar. 27, 2020, provisional application No. 63/001,017, filed on Mar. 27, 2020, provisional application No. 63/001,010, filed on Mar. 27, 2020.

(51) Int. Cl.
| | |
|---|---|
| *G06V 20/20* | (2022.01) |
| *G06T 11/00* | (2006.01) |
| *G06T 5/50* | (2006.01) |
| *G06T 13/40* | (2011.01) |
| *G16H 70/40* | (2018.01) |
| *G06N 5/02* | (2006.01) |
| *G06K 9/62* | (2022.01) |
| *G06V 20/62* | (2022.01) |
| *G06V 30/10* | (2022.01) |

(52) U.S. Cl.
CPC ............ *G06V 20/20* (2022.01); *G06K 9/6261* (2013.01); *G06N 5/02* (2013.01); *G06T 5/50* (2013.01); *G06T 11/00* (2013.01); *G06T 13/40* (2013.01); *G06V 20/63* (2022.01); *G16H 70/40* (2018.01); *G06T 2207/20221* (2013.01); *G06V 30/10* (2022.01)

(58) Field of Classification Search
CPC ........ G06V 20/20; G06V 20/63; G06V 30/10; G06V 30/141; G06K 9/6261; G06N 5/02; G06N 20/00; G06T 5/50; G06T 11/00; G06T 13/40; G06T 2207/20221; G06T 11/60; G16H 70/40; G16H 10/20; G16H 20/10; G16H 50/20; G16H 40/67
See application file for complete search history.

(56) References Cited

U.S. PATENT DOCUMENTS

| | | | |
|---|---|---|---|
| 2015/0286888 A1* | 10/2015 | Maison | G06V 20/20 382/182 |
| 2016/0267357 A1* | 9/2016 | Smith | G16Z 99/00 |
| 2019/0228854 A1* | 7/2019 | Jain | G06Q 30/0281 |

* cited by examiner

*Primary Examiner* — Jennifer Mehmood
*Assistant Examiner* — Andrew Shin
(74) *Attorney, Agent, or Firm* — Procopio, Cory, Hargreaves & Savitch LLP (57) ABSTRACT

A method for optical character recognition of text and information on a curved surface, comprising: activating an image capture device; scanning of the surface using the image capture device in order to acquire a plurality of scans of sections of the surface; performing OCR on the plurality of scans; separating the OCRed content into layers for each of the plurality of scans; merging the separated layers into single layers; and merging the single layers into an image.

4 Claims, 10 Drawing Sheets

SYSTEMS AND METHODS FOR OPTICAL CHARACTER RECOGNITION OF TEXT AND INFORMATION ON A CURVED SURFACE

CROSS-REFERENCE TO RELATED APPLICATION(S)

This application claims the benefit of U.S. Provisional Application Ser. No. 63/001,002, filed Mar. 27, 2020, U.S. Provisional Application Ser. No. 63/001,010, filed Mar. 27, 2020, U.S. Provisional Application Ser. No. 63/001,017, filed Mar. 27, 2020, U.S. Provisional Application Ser. No. 63/001,058, filed Mar. 27, 2020, which are expressly incorporated by reference herein their entirety.

BACKGROUND

1. Technical Field

The embodiments described herein are related to a platform that enables cost-effective medication adherence, and more specifically to voice-interactive avatar-guided systems and methods for prescription medication management.

2. Related Art

Medication non-adherence is a major challenge faced by the U.S. healthcare system, contributing to overspending on healthcare-related products and services by $300 billion per year. Medication adherence, defined as "taking medication properly and as prescribed by a physician," is a primary determinant to successful patient outcomes. Proper adherence to medication schedules is critical for improving health outcomes for problems such as hypertension, cardiovascular diseases, diabetes, arthritis, depression, lipid disorders, and many others. Unfortunately, recent data suggests that only around 50% of the 180 million U.S. patients with chronic conditions take their medications as directed. This problem is particularly acute among elderly patients, and those challenged with visual and cognitive challenges.

SUMMARY

Systems and methods for a mobile platform for patients and caregivers that provides voice-interactive patient guidance through a 3D animated character avatar in order to increase patient engagement, medical comprehension, and safety during drug therapy are described herein.

According to one aspect, a system comprises one or more processors configured to execute instructions, the instructions configured to cause the one or more processors to implement: multi-factor imaging and context-based optical character recognition for capturing prescription label content on a curved surface; conversational artificial intelligence (AI) for real-time verbal question and answer interactions with a user regarding at least some of: medications, drug schedules, contraindications, and capture patient input on medication use and effectiveness; and computer vision to quickly and accurately recognize a patient's pill with every dose taken and validating the medication based thereon These and other features, aspects, and embodiments are described below in the section entitled "Detailed Description."

BRIEF DESCRIPTION OF THE DRAWINGS

Features, aspects, and embodiments are described in conjunction with the attached drawings, in which.

DETAILED DESCRIPTION

The embodiments described herein are directed to systems and methods that enable a full-fledged conversational exchange between the patient and an adaptive personality Artificial Intelligence (AI), i.e., and avatar. This advancement uses a combination of speech biometric modalities and artificial neural networks to create a high-functioning avatar presence that will engage the patient and respond appropriately based on recognition of user voice characteristics (including inflections, patterns, and emotions), as well as behavioral cues, and predictive preferences. The adaptive personality AI will integrate personalized health information, medication history, and prescription data into a highly engaging drug therapy experience that will motivate patients towards adherence, advance health literacy, collect valuable medication use data, and improve patient outcomes.

Figure 10:
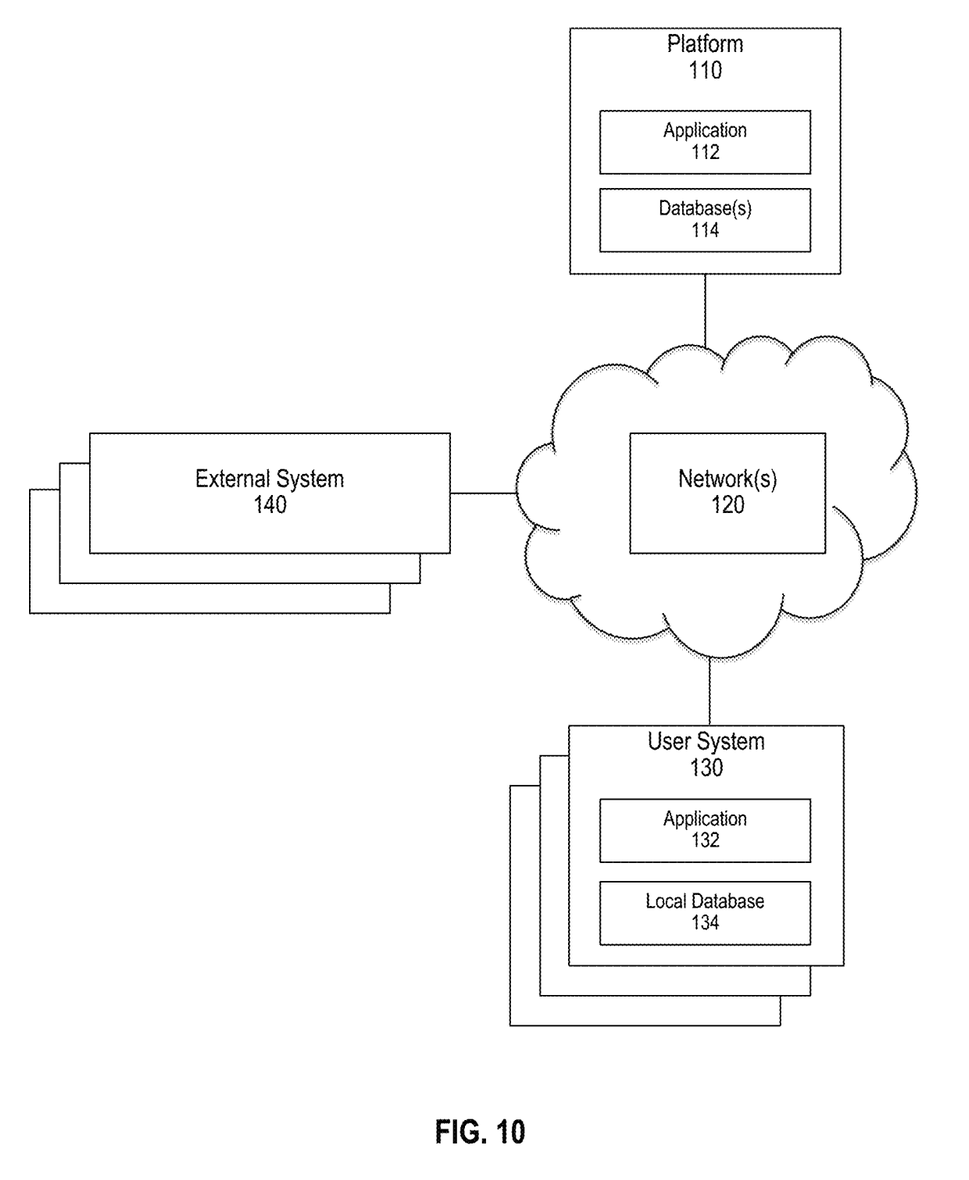
FIG. 10 is a diagram illustrating an example infrastructure in which one or more of the disclosed processes may be implemented, according to an embodiment.

FIG. 10 illustrates an example infrastructure in which one or more of the disclosed processes may be implemented, according to an embodiment. The infrastructure may comprise a platform 110 (e.g., one or more servers) which hosts and/or executes one or more of the various functions, processes, methods, and/or software modules described herein. Platform 110 may comprise dedicated servers, or may instead comprise cloud instances, which utilize shared resources of one or more servers. These servers or cloud instances may be collocated and/or geographically distributed. Platform 110 may also comprise or be communicatively connected to a server application 112 and/or one or more databases 114. In addition, platform 110 may be communicatively connected to one or more user systems 130 via one or more networks 120. Platform 110 may also be communicatively connected to one or more external systems 140 (e.g., other platforms, websites, etc.) via one or more networks 120.

Network(s) 120 may comprise the Internet, and platform 110 may communicate with user system(s) 130 through the Internet using standard transmission protocols, such as HyperText Transfer Protocol (HTTP), HTTP Secure (HTTPS), File Transfer Protocol (FTP), FTP Secure (FTPS), Secure Shell FTP (SFTP), and the like, as well as proprietary protocols. While platform 110 is illustrated as being connected to various systems through a single set of network(s) 120, it should be understood that platform 110 may be connected to the various systems via different sets of one or more networks. For example, platform 110 may be connected to a subset of user systems 130 and/or external systems 140 via the Internet, but may be connected to one or more other user systems 130 and/or external systems 140 via an intranet. Furthermore, while only a few user systems 130 and external systems 140, one server application 112, and one set of database(s) 114 are illustrated, it should be understood that the infrastructure may comprise any number of user systems, external systems, server applications, and databases.

User system(s) 130 may comprise any type or types of computing devices capable of wired and/or wireless communication, including without limitation, desktop computers, laptop computers, tablet computers, smart phones or other mobile phones, servers, game consoles, televisions, set-top boxes, electronic kiosks, point-of-sale terminals, Automated Teller Machines, and/or the like.

Platform 110 may comprise web servers which host one or more websites and/or web services. In embodiments in which a website is provided, the website may comprise a graphical user interface, including, for example, one or more screens (e.g., webpages) generated in HyperText Markup Language (HTML) or other language. Platform 110 transmits or serves one or more screens of the graphical user interface in response to requests from user system(s) 130. In some embodiments, these screens may be served in the form of a wizard, in which case two or more screens may be served in a sequential manner, and one or more of the sequential screens may depend on an interaction of the user or user system 130 with one or more preceding screens. The requests to platform 110 and the responses from platform 110, including the screens of the graphical user interface, may both be communicated through network(s) 120, which may include the Internet, using standard communication protocols (e.g., HTTP, HTTPS, etc.). These screens (e.g., webpages) may comprise a combination of content and elements, such as text, images, videos, animations, references (e.g., hyperlinks), frames, inputs (e.g., textboxes, text areas, checkboxes, radio buttons, drop-down menus, buttons, forms, etc.), scripts (e.g., JavaScript), and the like, including elements comprising or derived from data stored in one or more databases (e.g., database(s) 114) that are locally and/or remotely accessible to platform 110. Platform 110 may also respond to other requests from user system(s) 130.

Platform 110 may further comprise, be communicatively coupled with, or otherwise have access to one or more database(s) 114. For example, platform 110 may comprise one or more database servers which manage one or more databases 114. A user system 130 or server application 112 executing on platform 110 may submit data (e.g., user data, form data, etc.) to be stored in database(s) 114, and/or request access to data stored in database(s) 114. Any suitable database may be utilized, including without limitation MySQL™, Oracle™, IBM™, Microsoft SQL™, Access™, PostgreSQL™, and the like, including cloud-based databases and proprietary databases. Data may be sent to platform 110, for instance, using the well-known POST request supported by HTTP, via FTP, and/or the like. This data, as well as other requests, may be handled, for example, by server-side web technology, such as a servlet or other software module (e.g., comprised in server application 112), executed by platform 110.

In embodiments in which a web service is provided, platform 110 may receive requests from external system(s) 140, and provide responses in eXtensible Markup Language (XML), JavaScript Object Notation (JSON), and/or any other suitable or desired format. In such embodiments, platform 110 may provide an application programming interface (API) which defines the manner in which user system(s) 130 and/or external system(s) 140 may interact with the web service. Thus, user system(s) 130 and/or external system(s) 140 (which may themselves be servers), can define their own user interfaces, and rely on the web service to implement or otherwise provide the backend processes, methods, functionality, storage, and/or the like, described herein. For example, in such an embodiment, a client application 132 executing on one or more user system(s) 130 may interact with a server application 112 executing on platform 110 to execute one or more or a portion of one or more of the various functions, processes, methods, and/or software modules described herein. Client application 132 may be "thin," in which case processing is primarily carried out server-side by server application 112 on platform 110. A basic example of a thin client application 132 is a browser application, which simply requests, receives, and renders webpages at user system(s) 130, while server application 112 on platform 110 is responsible for generating the webpages and managing database functions. Alternatively, the client application may be "thick," in which case processing is primarily carried out client-side by user system(s) 130. It should be understood that client application 132 may perform an amount of processing, relative to server application 112 on platform 110, at any point along this spectrum between "thin" and "thick," depending on the design goals of the particular implementation. In any case, the application described herein, which may wholly reside on either platform 110 (e.g., in which case server application 112 performs all processing) or user system(s) 130 (e.g., in which case client application 132 performs all processing) or be distributed between platform 110 and user system(s) 130 (e.g., in which case server application 112 and client application 132 both perform processing), can comprise one or more executable software modules that implement one or more of the processes, methods, or functions of the application described herein.

Figure 9:
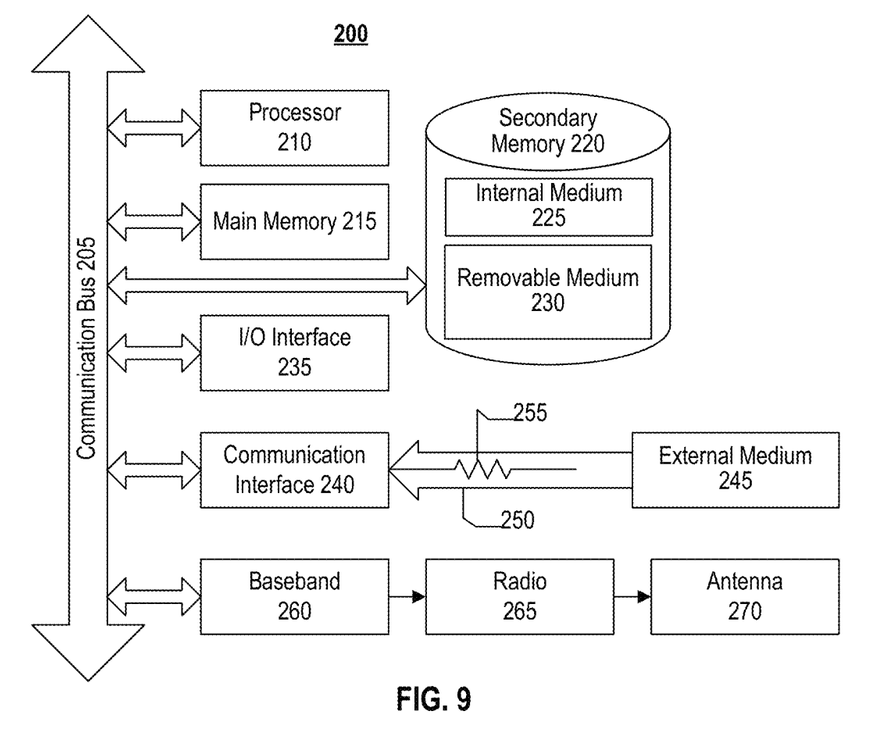
FIG. 9 is a block diagram illustrating an example wired or wireless system that can be used in connection with various embodiments described herein.

FIG. 9 is a block diagram illustrating an example wired or wireless system 200 that may be used in connection with various embodiments described herein. For example, system 200 may be used as or in conjunction with one or more of the functions, processes, or methods (e.g., to store and/or execute the application or one or more software modules of the application) described herein, and may represent components of platform 110, user system(s) 130, external system(s) 140, and/or other processing devices described herein. System 200 can be a server or any conventional personal computer, or any other processor-enabled device that is capable of wired or wireless data communication. Other computer systems and/or architectures may be also used, as will be clear to those skilled in the art.

System 200 preferably includes one or more processors, such as processor 210. Additional processors may be provided, such as an auxiliary processor to manage input/output, an auxiliary processor to perform floating-point mathematical operations, a special-purpose microprocessor having an architecture suitable for fast execution of signal-processing algorithms (e.g., digital-signal processor), a slave processor subordinate to the main processing system (e.g., back-end processor), an additional microprocessor or controller for dual or multiple processor systems, and/or a coprocessor. Such auxiliary processors may be discrete processors or may be integrated with processor 210. Examples of processors which may be used with system 200 include, without limitation, the Pentium® processor, Core i7® processor, and Xeon® processor, all of which are available from Intel Corporation of Santa Clara, Calif.

Processor 210 is preferably connected to a communication bus 205. Communication bus 205 may include a data channel for facilitating information transfer between storage and other peripheral components of system 200. Furthermore, communication bus 205 may provide a set of signals used for communication with processor 210, including a data bus, address bus, and/or control bus (not shown). Communication bus 205 may comprise any standard or non-standard bus architecture such as, for example, bus architectures compliant with industry standard architecture (ISA), extended industry standard architecture (EISA), Micro Channel Architecture (MCA), peripheral component interconnect (PCI) local bus, standards promulgated by the Institute of Electrical and Electronics Engineers (IEEE) including IEEE 488 general-purpose interface bus (GPIB), IEEE 696/S-100, and/or the like.

System 200 preferably includes a main memory 215 and may also include a secondary memory 220. Main memory 215 provides storage of instructions and data for programs executing on processor 210, such as one or more of the functions and/or modules discussed herein. It should be understood that programs stored in the memory and executed by processor 210 may be written and/or compiled according to any suitable language, including without limitation C/C++, Java, JavaScript, Perl, Visual Basic, .NET, and the like. Main memory 215 is typically semiconductor-based memory such as dynamic random access memory (DRAM) and/or static random access memory (SRAM). Other semiconductor-based memory types include, for example, synchronous dynamic random access memory (SDRAM), Rambus dynamic random access memory (RDRAM), ferroelectric random access memory (FRAM), and the like, including read only memory (ROM).

Secondary memory 220 may optionally include an internal medium 225 and/or a removable medium 230. Removable medium 230 is read from and/or written to in any well-known manner. Removable storage medium 230 may be, for example, a magnetic tape drive, a compact disc (CD) drive, a digital versatile disc (DVD) drive, other optical drive, a flash memory drive, and/or the like.

Secondary memory 220 is a non-transitory computer-readable medium having computer-executable code (e.g., disclosed software modules) and/or other data stored thereon. The computer software or data stored on secondary memory 220 is read into main memory 215 for execution by processor 210.

In alternative embodiments, secondary memory 220 may include other similar means for allowing computer programs or other data or instructions to be loaded into system 200. Such means may include, for example, a communication interface 240, which allows software and data to be transferred from external storage medium 245 to system 200. Examples of external storage medium 245 may include an external hard disk drive, an external optical drive, an external magneto-optical drive, and/or the like. Other examples of secondary memory 220 may include semiconductor-based memory, such as programmable read-only memory (PROM), erasable programmable read-only memory (EPROM), electrically erasable read-only memory (EEPROM), and flash memory (block-oriented memory similar to EEPROM).

As mentioned above, system 200 may include a communication interface 240. Communication interface 240 allows software and data to be transferred between system 200 and external devices (e.g. printers), networks, or other information sources. For example, computer software or executable code may be transferred to system 200 from a network server (e.g., platform 110) via communication interface 240. Examples of communication interface 240 include a built-in network adapter, network interface card (NIC), Personal Computer Memory Card International Association (PCMCIA) network card, card bus network adapter, wireless network adapter, Universal Serial Bus (USB) network adapter, modem, a wireless data card, a communications port, an infrared interface, an IEEE 1394 fire-wire, and any other device capable of interfacing system 200 with a network (e.g., network(s) 120) or another computing device. Communication interface 240 preferably implements industry-promulgated protocol standards, such as Ethernet IEEE 802 standards, Fiber Channel, digital subscriber line (DSL), asynchronous digital subscriber line (ADSL), frame relay, asynchronous transfer mode (ATM), integrated digital services network (ISDN), personal communications services (PCS), transmission control protocol/Internet protocol (TCP/IP), serial line Internet protocol/point to point protocol (SLIP/PPP), and so on, but may also implement customized or non-standard interface protocols as well.

Software and data transferred via communication interface 240 are generally in the form of electrical communication signals 255. These signals 255 may be provided to communication interface 240 via a communication channel 250. In an embodiment, communication channel 250 may be a wired or wireless network (e.g., network(s) 120), or any variety of other communication links. Communication channel 250 carries signals 255 and can be implemented using a variety of wired or wireless communication means including wire or cable, fiber optics, conventional phone line, cellular phone link, wireless data communication link, radio frequency ("RF") link, or infrared link, just to name a few.

Computer-executable code (e.g., computer programs, such as the disclosed application, or software modules) is stored in main memory 215 and/or secondary memory 220. Computer programs can also be received via communication interface 240 and stored in main memory 215 and/or secondary memory 220. Such computer programs, when executed, enable system 200 to perform the various functions of the disclosed embodiments as described elsewhere herein.

In this description, the term "computer-readable medium" is used to refer to any non-transitory computer-readable storage media used to provide computer-executable code and/or other data to or within system 200. Examples of such media include main memory 215, secondary memory 220 (including internal memory 225, removable medium 230, and external storage medium 245), and any peripheral device communicatively coupled with communication interface 240 (including a network information server or other network device). These non-transitory computer-readable media are means for providing executable code, programming instructions, software, and/or other data to system 200.

In an embodiment that is implemented using software, the software may be stored on a computer-readable medium and loaded into system 200 by way of removable medium 230, I/O interface 235, or communication interface 240. In such an embodiment, the software is loaded into system 200 in the form of electrical communication signals 255. The software, when executed by processor 210, preferably causes processor 210 to perform one or more of the processes and functions described elsewhere herein.

In an embodiment, I/O interface 235 provides an interface between one or more components of system 200 and one or more input and/or output devices. Example input devices include, without limitation, sensors, keyboards, touch screens or other touch-sensitive devices, biometric sensing devices, computer mice, trackballs, pen-based pointing devices, and/or the like. Examples of output devices include, without limitation, other processing devices, cathode ray tubes (CRTs), plasma displays, light-emitting diode (LED) displays, liquid crystal displays (LCDs), printers, vacuum fluorescent displays (VFDs), surface-conduction electron-emitter displays (SEDs), field emission displays (FEDs), and/or the like. In some cases, an input and output device may be combined, such as in the case of a touch panel display (e.g., in a smartphone, tablet, or other mobile device).

System 200 may also include optional wireless communication components that facilitate wireless communication over a voice network and/or a data network (e.g., in the case of user system 130). The wireless communication components comprise an antenna system 270, a radio system 265, and a baseband system 260. In system 200, radio frequency (RF) signals are transmitted and received over the air by antenna system 270 under the management of radio system 265.

In an embodiment, antenna system 270 may comprise one or more antennae and one or more multiplexors (not shown) that perform a switching function to provide antenna system 270 with transmit and receive signal paths. In the receive path, received RF signals can be coupled from a multiplexor to a low noise amplifier (not shown) that amplifies the received RF signal and sends the amplified signal to radio system 265.

In an alternative embodiment, radio system 265 may comprise one or more radios that are configured to communicate over various frequencies. In an embodiment, radio system 265 may combine a demodulator (not shown) and modulator (not shown) in one integrated circuit (IC). The demodulator and modulator can also be separate components. In the incoming path, the demodulator strips away the RF carrier signal leaving a baseband receive audio signal, which is sent from radio system 265 to baseband system 260.

If the received signal contains audio information, then baseband system 260 decodes the signal and converts it to an analog signal. Then the signal is amplified and sent to a speaker. Baseband system 260 also receives analog audio signals from a microphone. These analog audio signals are converted to digital signals and encoded by baseband system 260. Baseband system 260 also encodes the digital signals for transmission and generates a baseband transmit audio signal that is routed to the modulator portion of radio system 265. The modulator mixes the baseband transmit audio signal with an RF carrier signal, generating an RF transmit signal that is routed to antenna system 270 and may pass through a power amplifier (not shown). The power amplifier amplifies the RF transmit signal and routes it to antenna system 270, where the signal is switched to the antenna port for transmission.

Baseband system 260 is also communicatively coupled with processor 210, which may be a central processing unit (CPU). Processor 210 has access to data storage areas 215 and 220. Processor 210 is preferably configured to execute instructions (i.e., computer programs, such as the disclosed application, or software modules) that can be stored in main memory 215 or secondary memory 220. Computer programs can also be received from baseband processor 260 and stored in main memory 210 or in secondary memory 220, or executed upon receipt. Such computer programs, when executed, enable system 200 to perform the various functions of the disclosed embodiments.

Embodiments of processes for prescription medication management will now be described in detail. It should be understood that the described processes and systems, e.g., system 100, may be embodied in one or more software modules that are executed by one or more hardware processors (e.g., processor 210), for example, as the application discussed herein (e.g., server application 112, client application 132, and/or a distributed application comprising both server application 112 and client application 132), which may be executed wholly by processor(s) of platform 110, wholly by processor(s) of user system(s) 130, or may be distributed across platform 110 and user system(s) 130, such that some portions or modules of the application are executed by platform 110 and other portions or modules of the application are executed by user system(s) 130. The described processes may be implemented as instructions represented in source code, object code, and/or machine code. These instructions may be executed directly by hardware processor(s) 210, or alternatively, may be executed by a virtual machine operating between the object code and hardware processors 210. In addition, the disclosed application may be built upon or interfaced with one or more existing systems.

Alternatively, the described processes may be implemented as a hardware component (e.g., general-purpose processor, integrated circuit (IC), application-specific integrated circuit (ASIC), digital signal processor (DSP), field-programmable gate array (FPGA) or other programmable logic device, discrete gate or transistor logic, etc.), combination of hardware components, or combination of hardware and software components. To clearly illustrate the interchangeability of hardware and software, various illustrative components, blocks, modules, circuits, and steps are described herein generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a component, block, module, circuit, or step is for ease of description. Specific functions or steps can be moved from one component, block, module, circuit, or step to another without departing from the invention.

Furthermore, while the processes, described herein, are illustrated with a certain arrangement and ordering of subprocesses, each process may be implemented with fewer, more, or different subprocesses and a different arrangement and/or ordering of subprocesses. In addition, it should be understood that any subprocess, which does not depend on the completion of another subprocess, may be executed before, after, or in parallel with that other independent subprocess, even if the subprocesses are described or illustrated in a particular order.

Figure 1:
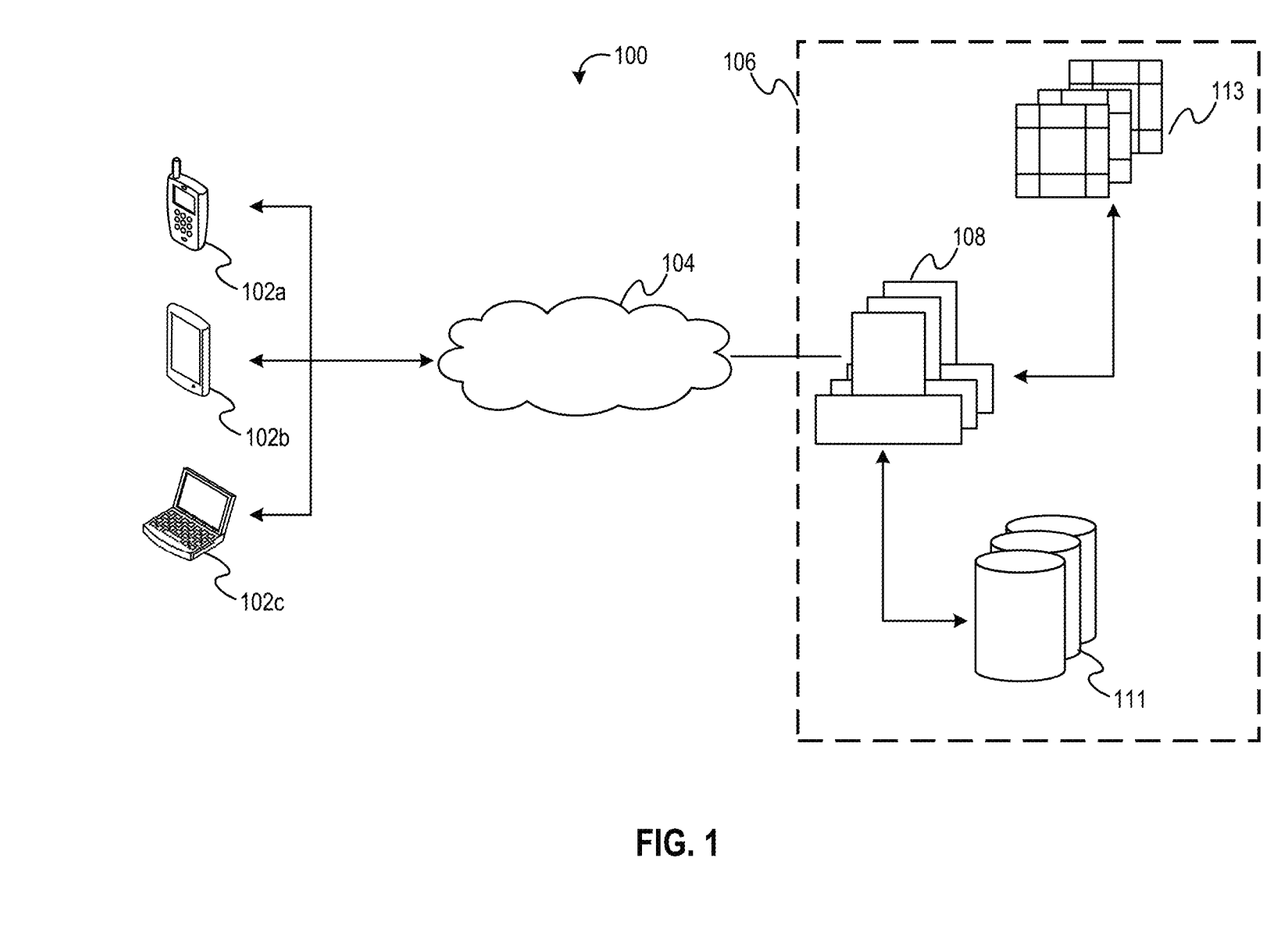
FIG. 1 is a diagram illustrating an example medication adherence system 100 configured in accordance with one example embodiment.

FIG. 1 is a diagram illustrating an example medication adherence system 100 configured in accordance with one example embodiment. As can be seen, system 100 comprises a backend platform 106, which can include all or some aspects of platform 110, that is configured to provide an adaptive personality AI experience that helps patients with medication adherence. Platform 106 can comprise one or more servers 108, co-located or remotely located, interfaced with one or more databases 111. As described below, databases 111 can store patient data, medication data, prescription data, pill image data, etc.

Platform 106 can also comprise a plurality of programs, instructions, algorithms, etc. (programs), 113 that enable the backend 106 to perform the functionality described herein. Programs 113 can include machine learning algorithms, computer vision algorithms, AI algorithms, etc.

Patients can then use their user device 102a, b, c, which can include some or all of the aspects of user system 130, to access platform 106 via a network 104. Example networks and network components are described below. User device 102 can be a mobile device such as a smartphone, tablet, smart watch, smart home device, wearable device, etc., or a personal computer such as a desktop or laptop computer. The user can download an application, or otherwise install or have the application installed on their device 102 that will allow them to access a User Interface (UI), which allows them to carry the workflows described herein and interact with platform 106.

The components of system 100, enable the system to implement or perform the following: $_1$) Multi-factor imaging and "context-based" optical character recognition methodology for capturing prescription label content on a curved surface (such as pill bottle) in order to quickly digitize and integrate label information into the application with no manual input from the user. 2) Conversational artificial intelligence (AI) embodied through a 3D animated character avatar, allowing for real-time verbal question and answer interactions with the patient regarding medications, drug schedules, contraindications, and capture patient input on medication use and effectiveness. 3) Pill image validation for every dose—A novel computer vision method for using a camera on a mobile device or wearable to quickly and accurately recognize a patient's pill with every dose taken, and collect and track that data. This method uses a unique combination of negative elimination and data augmentation techniques to significantly improve pill image recognition accuracy in order to provide a feasible solution for everyday pill validation. 4) Personalized augmented reality messaging (AR) and information—The system includes an AR module that allows the user of a mobile device or wearable to hold the device over or in front of a medication label and receive both personal and non-personal information and graphical indicators in virtual format overlaid over the live image. Messaging can include, but is not limited to, color-coding to help identify medication type/statuses, medication data, warnings about drug conflicts, refill date reminders, as well as doctor and pharmacy contact info. Personalized messages in text, image or video format from caregivers, pharmacists, doctors, and other healthcare providers, may also be overlaid.

Figure 2:
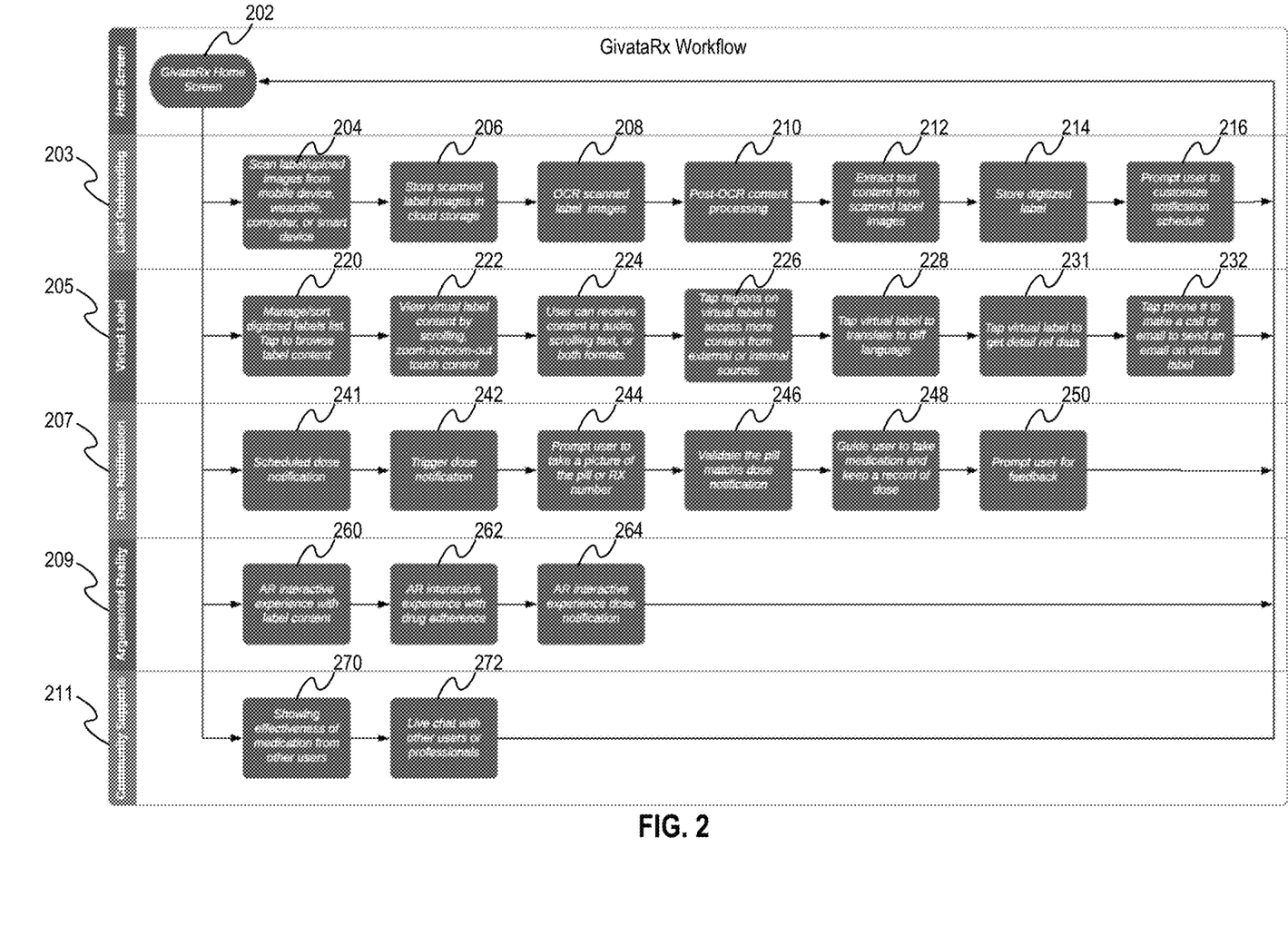
FIG. 2 is a diagram illustrating an example various workflows that are carried out by the platform and the application and user interface on the user device of the system of FIG. 1 in accordance with another example embodiment.

FIG. 2 is a diagram illustrating various workflows that are carried out by platform 106 and the application and user interface on the user device 102. As illustrated, the user can implement the following workflows, label onboarding 203, virtual label construction 205, dose notification 207, augmented reality 209, and community support 211.

The label onboarding workflow 203 can comprise scanning and uploading an image, using an image capture device, such as a camera (not shown) included in user device 102 in step 204. In step 206, the scanned image can be transmitted to platform 106 and stored in database(s) 110. Once stored, the algorithms 112 allow servers 108 to OCR the scanned labels in step 208, post-process the OCR content in step 210, and extract text content from the scanned images in step 212. This OCR process is where the Multi-factor imaging and "context-based" optical character recognition, which is described in more detail below, comes into play. The extracted text can then be stored, e.g., in databases 110 in step 214.

It should be noted that in certain embodiments, some or all of the steps associated with the label onboarding process can be performed on the user's device 102.

Further, label digitization can be enhanced using a feedback loop in which users' pill bottle label images are collected and used to improve the algorithm for classifying data types and adapting post-OCR processing (step 210) techniques to new or newly updated label types. In other words, as labels are scanned and processed, the information contained in the scans can be used to help improve recognition and digitization of newly scanned labels.

In step 216, the user can be prompted, through the application UI to input or customize a notification schedule to be used in the dose notification workflow 207. The augment reality capability can be used throughout the onboarding workflow 203.

Figure 3:
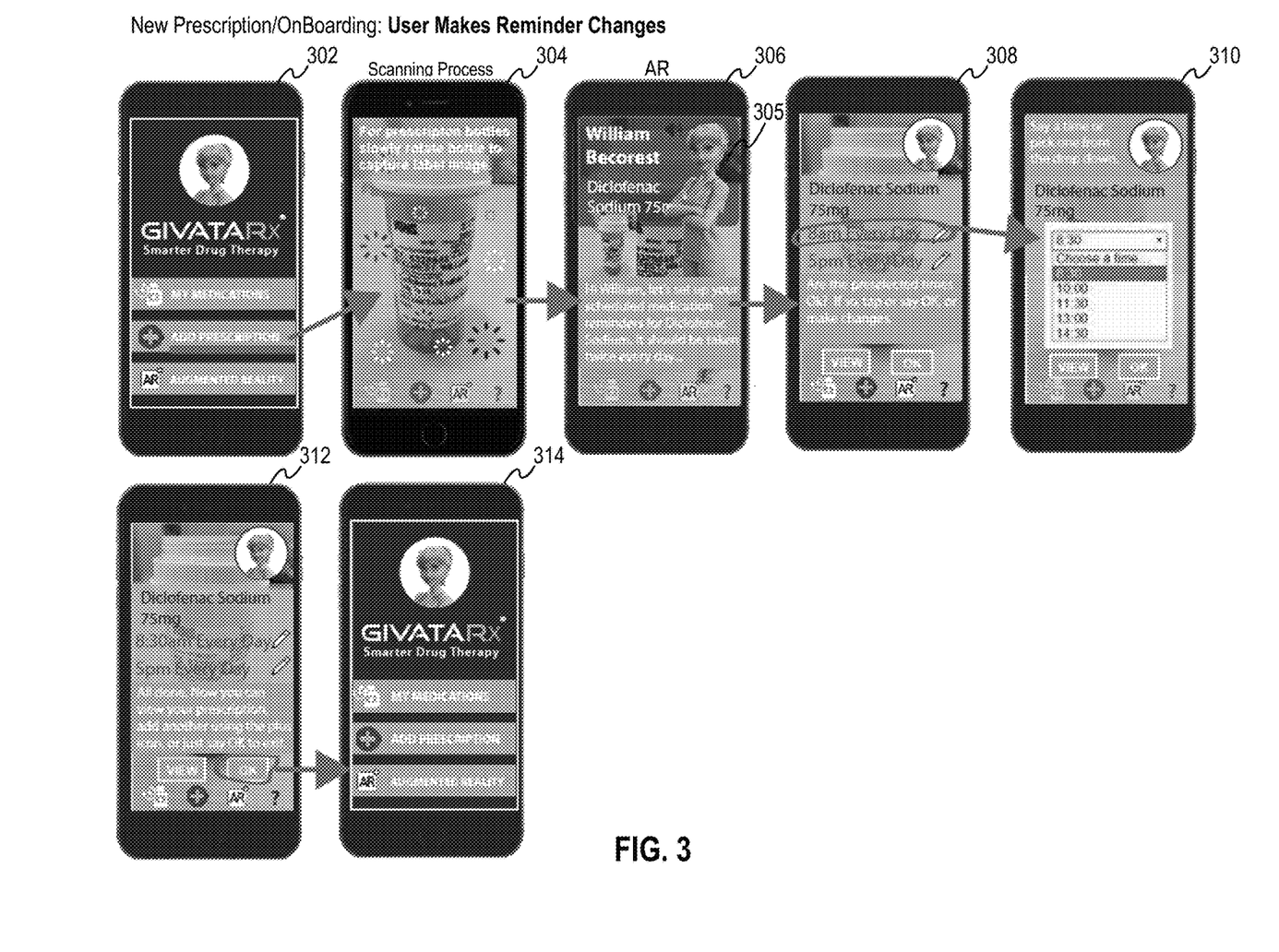
FIG. 3 illustrates a series of screen shots that can be implemented via the application UI on a device of the system of FIG. 1 during the onboarding workflow.

For example, FIG. 3 illustrates a series of screen shots that can be implemented via the application UI on a device 102 during the onboarding workflow 203. First, as illustrated in screen shot 302, the user can select to add a new prescription. This will cause the application to activate the device's camera in order to scan the medication label as illustrated in screen shot 304.

As can be seen, the label is curved, which presents issues for conventional OCR techniques. Moreover, different entities, e.g., pharmacies have different label formats, which can make it difficult with conventional techniques to identify critical data. The Multi-factor imaging and "context-based" optical character recognition described below with the feedback loop described above addresses these shortcomings of conventional techniques.

Once the data is extracted from the label, the user can be prompted (step 216) via the AI, e.g., as embodied by avatar 305, to update or provide a notification schedule. As illustrated in screen shot 306, avatar 305 can prompt the user via voice communication to schedule reminders. The prompt can also, or in the alternative be provided via text as well, e.g., to ensure any users with hearing problems can still understand the prompt. As noted, the system 100 can determine based on the label data, how often the user is supposed to take the medication. Thus, the AI can suggest appropriate times and allow the user to select or change the times as illustrated in screenshots 308 and 310.

The user can then be prompted, if needed to add other prescriptions as illustrated in screenshots 312 and 314.

Figure 4:
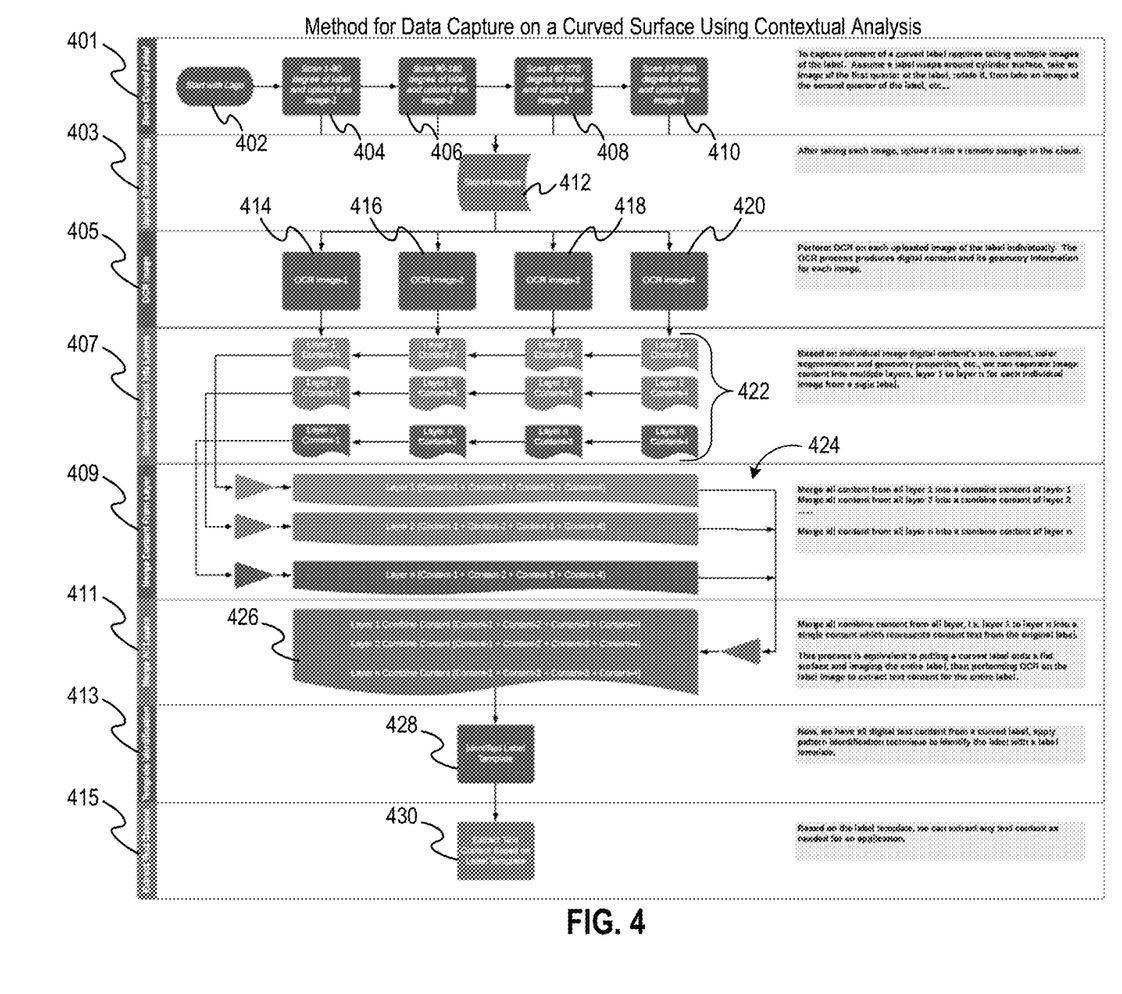
FIG. 4 is a diagram illustrating a process for imaging a curved surface in accordance with one example embodiment.

As noted above, imaging the curved surface of the pill container, or any curved surface, presents problems for conventional OCR techniques. FIG. 4 is a diagram illustrating a process for imaging a curved surface in accordance with one example embodiment. As can be seen, the process comprises scanning the curved label, in several sections, in step 401 and then uploading, e.g., the platform 106, the scanned images in step 403. Persistent scanning can be used to obtain the section images.

Capturing the medication label data images by using a mobile device's camera can comprise taking a photo, rotating the pill bottle, taking another photo, rotate, etc., until the entire label is represented within 3-4 images. Alternatively, video capture allows the user to move the camera around the label, or rotate the pill bottle with label in front of a camera, capturing the image on video in one continuous movement. As a result, the system captures a multitude of image frames and selects out the best frames for use in the post-OCR process of identifying data, ensuring accuracy, and placing it in the proper fields. The application will control the camera and segment the received video frame images into the appropriate sections.

OCR accuracy is highly dependent on image quality. Images with OCR targets that are blurry, off-center, askew, poorly lit, too close to the camera, too far from the camera, etc., often result in poor OCR results. This is an important challenge for any system that utilizes OCR, and especially for the a system, such as described herein that captures prescription label content on curved or uneven surfaces (such as prescription pill bottles). To ensure the best possible OCR outcome, system 100 can implement an onscreen guidance methodology to help users ensure the best possible image quality in order to facilitate optimal OCR results. This methodology can include: 1) a visual calibration system including, e.g., 3 graphical dots or some other symbol(s) overlaid onscreen in real time as the user positions the device or the prescription label. The graphical dots may be one color (such as white or red) until such time that the user has positioned the device or the prescription label into the ideal position for image capture. At that point the graphical dots turn in color (to green for example) to indicate the user has found the ideal positioning. This event triggers the device auto focus and auto capture of the image; 2) an algorithm that defines the ideal distance and positioning for the device in relation to the image object by triangulating an ideal planular distance to each of the calibration dots or symbols. This ensures the most parallel possible positioning between object and device camera; and 3) A voice guidance component aids the user in this process by providing directional help ("move closer," "back up," "hold steady," etc.) and environmental recommendations ("lighting is too dark, please correct", etc.).

The images of the sections can then be OCRed in step 405 and separated in to layers in step 407. The content from the different sections can then be merged by layer in step 409 and then merged into one image in step 411.

Platform 106 can then recognize that the label fits a certain template, e.g., through the feedback loop and machine learning, in step 413. This allows the platform 106 to extract the label data based on the associated template in step 415. The data can then be populated, e.g., in a database 114 that allows platform 106 to access and present the data in an appropriate manner, e.g., as illustrated in the screen shots of FIG. 5.

Returning to FIG. 4 in more detail, the user can be instructed to start with the logo on the label and begin the scan, either capturing individual sections of the label or by simply scabbing the label with the camera and allowing the video function to capture the required images (steps 404-410). The video function can capture images, perform tests to ensure that the capture images are of sufficient quality and then use the best, or sufficient images and store them 412.

In steps 414-420 the stored images can then be OCRed and then separated into layers in step 422. In step 424, the layers can be merged across the images and then the layers can be merged, in step 426 into a single image that can then be compared to a plurality of label templates in step 428. Once the template is identified, then data or information can be extracted from the image of step 426 and stored in a database for later retrieval.

Figure 5:
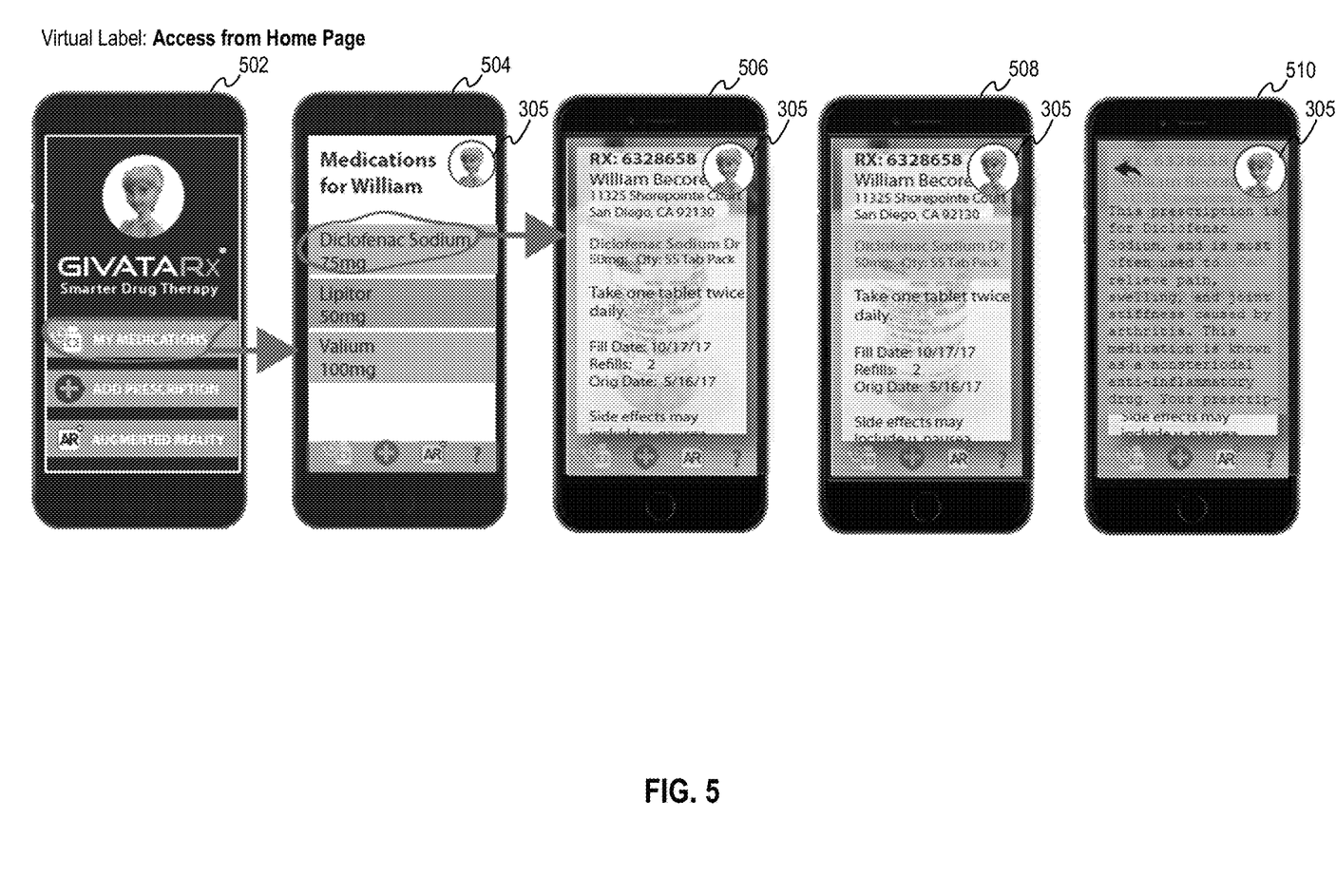
FIG. 5 illustrates a series of screen shots that can be implemented via the application UI on a device of the system of FIG. 1 for displaying and interacting with a virtual label.

Each onboarded medication can now have its own "virtual label" that can be interacted with as illustrated by the workflow of FIG. 2 and the screen shots of FIG. 5. Referring back to FIG. 2, the virtual label workflow 205 allows the user to manage and sort labels in step 220, view virtual content in step 222 as well as receive audio, scrolling text or both in step 224. In step 226 the user can tap various areas of the virtual label and access information related to the medication as illustrated with respect to FIG. 5.

Figure 8:
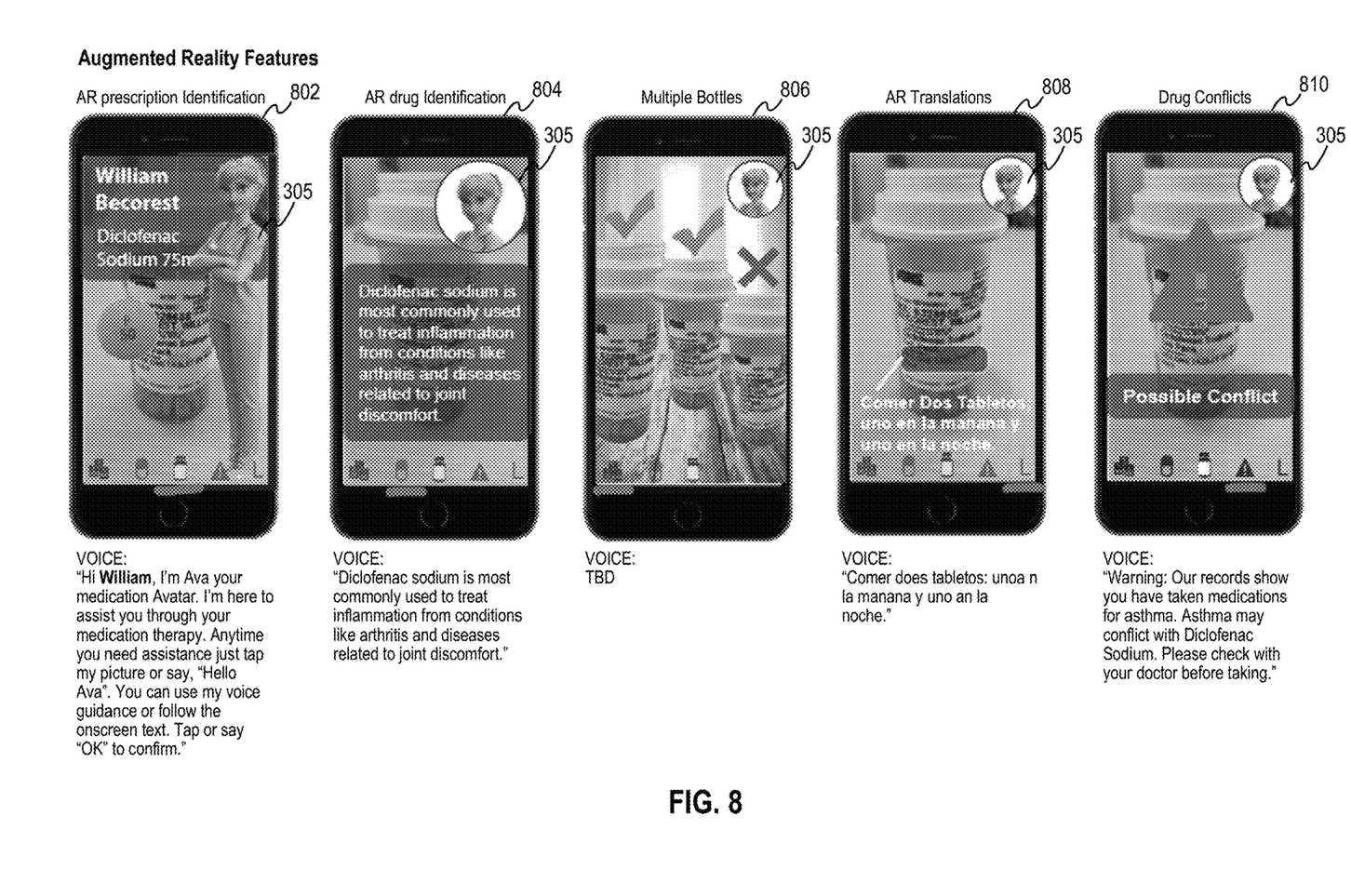
FIG. 8 are screen shots associated with the augmented reality capabilities within the systems of FIG. 1.

As illustrated with respect to FIG. 8, the augmented reality capability also allows the user to translate portions of the virtual label (step 228). The user can also interact with the virtual label to get reference data (step 231) and to generate a call or email to contacts associated with the virtual label (step 232).

Some of these steps are illustrated with respect to FIG. 5. Thus, the user can select to access information about their medications as illustrated in screen shot 502. A list of the medications can then be shown as illustrated in screen shot 504. If the user selects one of the medications, then information such as the notification schedule can be shown as illustrated in screen shot 506.

Further information can also be available if the user chooses to access such information as illustrated in screen shots 508 and 510. The information displayed can come from label data as well as external databases, such as FDA and related sources via APIs.

Avatar 305 can provide voice feedback that reads the content aloud (unless user turns off audio) while matching text displays or scrolls on screen. The avatar 305 can also provide options and suggestions. Moreover, the user can interact with the UI via voice commands.

With respect to dose notification and validation workflow 206, the system can schedule the dose notifications as described above (step 241), which will trigger a dose notification through the UI at the appropriate day/time (step 242). The user can then be prompted to take a picture of the pill in step 244. The platform can then validate the pill and dose match the notification in step 246. The user can then be guided to take the dose and provide feedback in steps 248 and 250.

As noted below with respect to FIGS. 6 and 7, in other embodiments, the user can be allowed to image the label instead of the pill.

Figure 6:
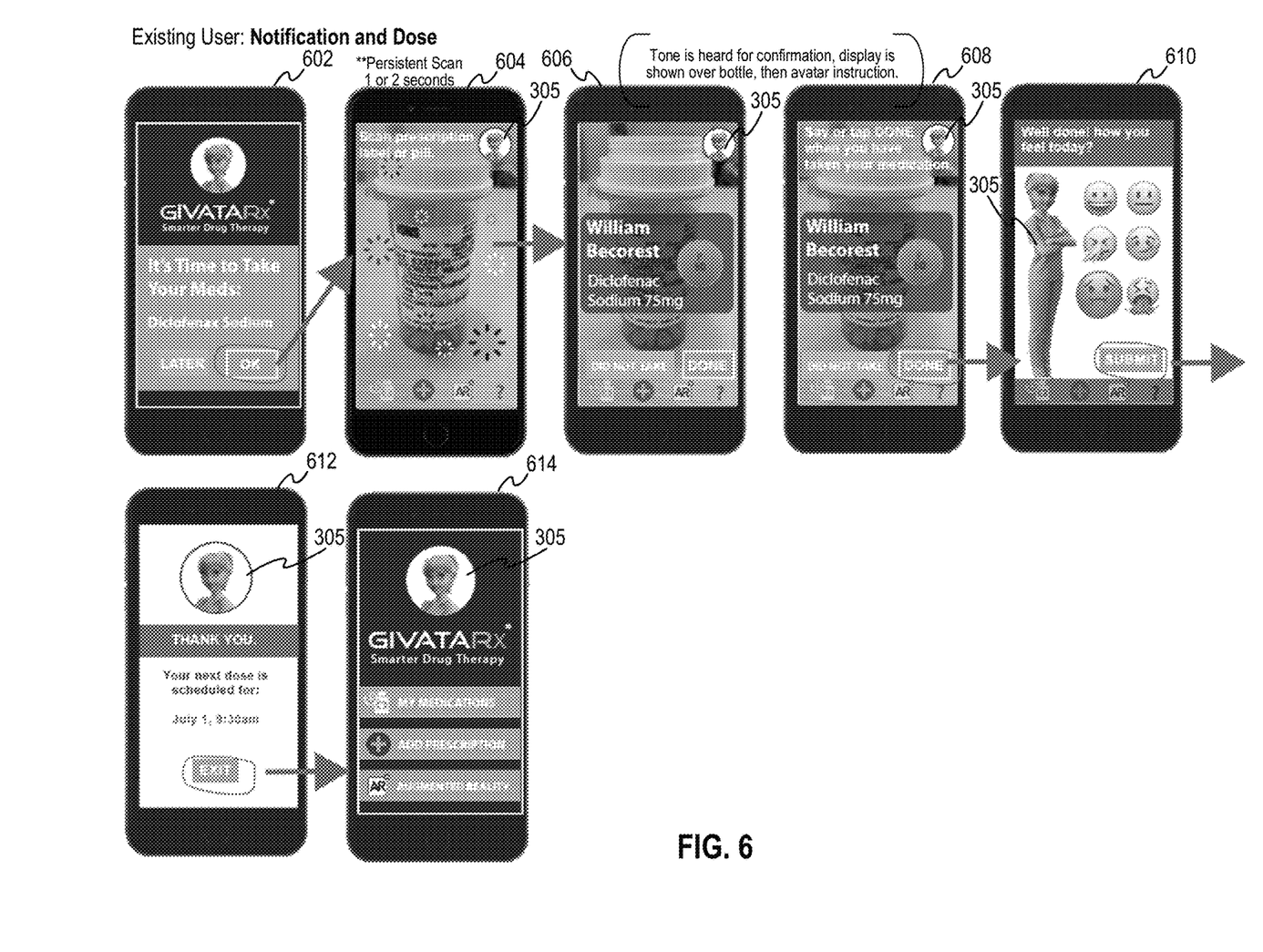
FIGS. 6 and 7 illustrate screen shots associated with two implementations of a dose notification workflow that can be implemented via the application UI on a device of the system of FIG. 1.
Figure 7:
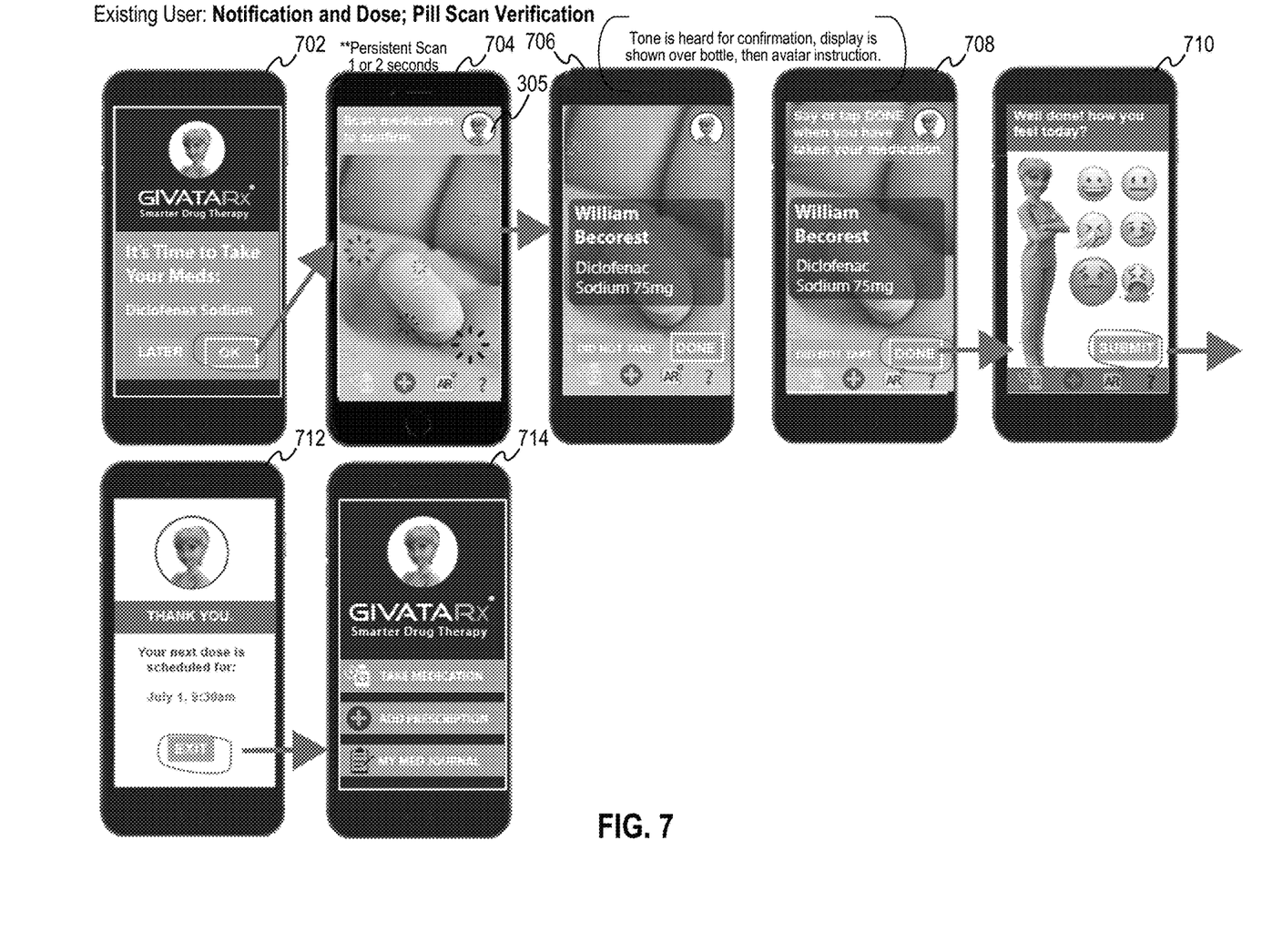

FIGS. 6 and 7 illustrate screen shots associated with two implementations of the dose notification workflow 207. For compliance there can be two user workflows, depending on what the user scans, e.g., the bottle or the pill? In the case of the bottle/label scan, the capture process is only looking for prescription number and/or name to verify as illustrated in FIG. 6.

As illustrated, if the user selects OK in response to a schedule notification as illustrated in screen shot 602, then the camera can be activated so the user can scan the label as illustrated in screen shot 604. The label can be scanned using the persistent scanning and OCR as described above with respect to FIG. 4.

As illustrated in screen shot 606, the medication can be identified for the user. In certain embodiments, a tone and/or avatar 305 confirmation can also be output once the medication is identified and confirmed. As illustrated in screenshots 608 and 610, the user can indicate they have taken the medication and can be prompted via the UI and/or avatar 305 to indicate how they are feeling. The user can then be reminded of their next scheduled dose, as illustrated in screenshot 612 and returned to the home screen as illustrated in screenshot 614.

If the user instead scans the pill, then the same basic workflow can be followed, with platform 106 recognizing the pill instead of the label information as illustrated in screenshots 702-714. But as mentioned, pill recognition has its own complications and difficulties. But as noted above, if the user has scanned the label and indicated a medication schedule, then platform 106 knows what pills the user should be taking at a given time. Thus, when the user scans the pill the platform can compare the scan/image to the stored image of the appropriate pill to confirm, using, e.g., a set of comparison criteria, the user has the correct pill.

It should be noted that pill recognition and validation can also implement a feedback loop in which user images of pills taken during the capture process are collected and added to the training data used to train, e.g., neural network that identifies and validates the pills. This continuous loop ensures continual expansion of the data set and improvement of the accuracy of the system's predictive outcomes.

Elderly patients suffering from a combination of chronic conditions, cognitive challenges, and deteriorating vision are among those patient groups most in need of accurate monitoring related to prescription drug management. For example, patients who suffer from cognitive impairments like memory loss are more likely than the general population to mix up two different, but similar-looking medications, mistakenly take a prescribed dose twice because of memory lapse, neglect to take prescriptions on time, and stop taking meds due to frustration or disengagement. As a consequence, pill image validation for every dose is especially beneficial for such patients and their caregivers by improving medication safety, and provides a tracking mechanism that could prolong patient independence, and improve caregiver oversight.

Universal pill image recognition has been an important topic of discovery over the last several years by NIH and others, but identification accuracy remains insufficient for everyday pill validation. A 2018 Microsoft Research-funded project correctly identified a pill in 74.4% of tests using Inception-v3, a pre-trained convolutional neural network. There remain many technical obstacles to achieving high levels of accuracy with pill image recognition. Variables like background type/color, lighting, camera type, angle, and imprint visibility present significant challenges to the recognition system when a user takes a picture of a pill or group of pills.

But within the constraints of medication adherence system 100, where medications are generally known for each patient user, a computer vision capability that uses a combination of negative elimination and data augmentation techniques makes it possible to significantly improve pill identification accuracy so that it can be used continuously as a pill validation step with every medication dose.

There are five main parts to the computer vision capability: 1) the mobile adherence application, or system, in which a list of patient medications are known, and which provides platform 106 from which the user engages the pill imaging process; 2) A "negative elimination" algorithm 112 that uses a-priori knowledge of individual patient medications to assign probabilities to any pill image being scanned by the patient user; 3) An image augmentation process using DeepAugment to apply various image augmentations to the data set; 4) Test-time augmentation (TTA), the process of making multiple augmented copies of the pill image when the pill(s) is scanned; 5) A Convolutional Neural Network (CNN) to which the results from the prior three processes are applied.

As noted, the AR workflow, or capability can be implemented as part of various workflows within system 100. The process is illustrated via steps 260-264 and screenshots and associated voice information for various workflows or process are illustrated in FIG. 8.

Platform 106 can also offer community feedback and support (workflow 211) in which the user can get feedback from other users (step 271) and even chat with other users or professionals through the application and platform 106 (step 272).

In certain embodiments, biological and medical data can be acquired before and/or after a user takes a pill(s) form various sensors and other input mechanisms, e.g., application 132. This data can be aggregated and compared to the data for other users to detect effects that are above or below a median, threshold, etc. A simple example, would be that data can be received form a blood pressure cuff a certain amount of time after a user has taken blood pressure medicine. The user could also provide information on how they "feel". This information can be compared to other users on the same or similar medicine, and same historical blood pressure to see how the user's blood pressure is being affected relative to the larger population. Since platform 106 also has information about other pills the user is taking, platform 106 can also determine whether certain combination of drugs impact the efficacy of individual drugs in the combination.

While certain embodiments have been described above, it will be understood that the embodiments described are by way of example only. Accordingly, the systems and methods described herein should not be limited based on the described embodiments. Rather, the systems and methods described herein should only be limited in light of the claims that follow when taken in conjunction with the above description and accompanying drawings.

What is claimed:

1. A system comprising:
one or more processors configured to execute instructions, the instructions configured to cause the one or more processors to implement:
multi-factor imaging and context-based optical character recognition for capturing prescription label content on a curved surface, wherein the multi-factor imaging and context-based optical character recognition comprises:
activating an image capture device;
scanning of the surface using the image capture device in order to acquire a plurality of scans of sections of the surface;
performing OCR on the plurality of scans;
separating the OCRed content into layers for each of the plurality of scans;
merging the separated layers into single layers; merging the single layers into an image,
identifying a template associated with the image, and extracting text and information from the image based on the identified template, and
storing the text and information in the form of a virtual label;
conversational artificial intelligence (AI) for real-time verbal question and answer interactions with a user regarding at least some of: medications, drug schedules, general health and wellbeing, contraindications, and capture patient input on medication use and effectiveness related to the virtual label; and computer vision via the image capture device to quickly and accurately recognize a patient's pill with every dose taken and validating the medication based thereon.

2. The system of claim 1, wherein the computer vision uses a combination of negative elimination and data augmentation to improve pill image recognition accuracy.

3. The system of claim 1, wherein the text and information include at least some of: color-coding to help identify medication type/statuses, medication data, warnings about drug conflicts, refill date reminders, doctor and pharmacy contact info, and personalized messages in text, image or video format from caregivers, pharmacists, doctors, and other healthcare providers.

4. The system of claim 1, wherein the instructions are further configured to cause the processor to implement at least one of the following workflows: label onboarding; creation of virtual label, dose notification, augmented reality, community support, and providing engagement with a health provider.

\* \* \* \* \*